United States Patent [19]

Tandon

[11] 4,243,412

[45] Jan. 6, 1981

[54] DENTAL ALLOY

[75] Inventor: Dinesh C. Tandon, Canton, Mich.

[73] Assignee: Sybron Corporation, Rochester, N.Y.

[21] Appl. No.: 46,325

[22] Filed: Jun. 7, 1979

[51] Int. Cl.³ ............................................. C22C 19/05
[52] U.S. Cl. .................................... 75/171; 433/200; 433/207
[58] Field of Search .................... 75/171, 170; 148/32, 148/32.5; 433/200, 207

[56] References Cited

U.S. PATENT DOCUMENTS

| | | | |
|---|---|---|---|
| 2,994,605 | 8/1961 | Gill et al. ................................ | 75/171 |
| 3,544,315 | 12/1970 | Asgar ...................................... | 75/171 |
| 3,749,570 | 7/1973 | Lyon ...................................... | 75/171 |
| 3,841,868 | 10/1974 | Dudek et al. ........................... | 75/171 |
| 3,914,867 | 10/1975 | Manning et al. ....................... | 75/171 |
| 3,948,653 | 4/1976 | Tesk et al. .............................. | 75/171 |

*Primary Examiner*—R. Dean
*Attorney, Agent, or Firm*—Theodore B. Roessel; Owen D. Marjama

[57] ABSTRACT

A nickel base dental alloy having the following composition:

| | Percent by Weight |
|---|---|
| Chromium | 10–20 |
| Molybdenum | 4–10 |
| Iron | 3–6 |
| Columbium | 2–6 |
| Aluminum | up to 2.0 |
| Silicon | 1.0–3.0 |
| Carbon | 0.05–0.5 |
| Nickel | Balance. |

5 Claims, No Drawings

DENTAL ALLOY

BACKGROUND OF THE INVENTION

This invention relates in general to a dental alloy and more specifically to a dental alloy having specific utility for use in porcelain to metal dental restorations.

A metal alloy for making a dental restoration must be strong, tough, resistant to tarnish, oxidation and corrosion, compatible with the human oral environment (biocompatible), have good castability and, if used with procelain, have a suitable coefficient of thermal expansion to be fusible to porcelain.

While many nickel alloys have been used in the dental profession with varying degrees of success, most of these alloys do not possess a combination of all of the above desirable properties.

It is therefore an object of this invention to provide a dental alloy suitable for procelain to metal restorations which provides optimum physical and mechanical properties, and outstanding handling characteristics.

SUMMARY OF THE INVENTION

The foregoing objects and others are accomplished in accordance with this invention by providing a new and novel dental alloy having particular utility for use in porcelain to metal dental restorations. With respect to the alloy composition, all percentages are in weight percent.

The alloy is essentially a nickel base alloy which contains a significant amount of chrominum and smaller but significant amounts of molybdenum, iron, columbium, aluminum, silicon and carbon. It should be understood that the alloy also may include small amounts of impurities and trace amounts of other elements normally asociated with compositions of this type. The broad composition range of the alloy is as follows:

|  | Percent by Weight |
|---|---|
| Chromium | 10–20 |
| Molybdenum | 4–10 |
| Iron | 3–6 |
| Columbium | 2–6 |
| Aluminum | up to 2.0 |
| Silicon | 1.0–3.0 |
| Carbon | 0.05–0.5 |
| Nickel | Balance. |

DETAILED DESCRIPTION OF THE INVENTION

The alloy described herein represents a major advance in the development of an alloy for use in porcelain to metal dental restorations. Whereas many nickel alloys have been used in the dental profession in the past and have been known to possess one or the other of the desirable properties, the alloy of the present invention incorporates improved properties of melting, casting, finishing, porcelain compatability, and soldering, for a porcelain crown and bridge alloy. Specifically, the alloy of the present invention exhibits the following properties all in one alloy composition:

The alloy can be cast by either the oxygen and gas torch or induction melting technique. The alloy possesses much lower hardness than many alloys available commercially. When compared to commercially available alloys the hardness of the alloy of this invention offers significant improvements. Unlike the other alloys of lower hardness, the alloy of the present invention does not react with the ceramic melting crucible during normal torch melting procedures. This is due to lower alloy susceptibility to overheating during torch melting. This resistance to overheating and to a reaction with the crucible reduces the occurance of inclusions in the resultant castings, and the alloy thus maintains its physical properties during subsequent operations.

The alloy also possesses improved fluidity thereby making it easier to observe and determine the point during the melting at which the casting is to be made. The increased fluidity thus reduces the chance of overheating the alloy thereby destroying the alloy properties, and reduces the possibility of the formation of inclusions by preventing an alloy reaction with the ceramic crucible.

The alloy exhibits excellent burnishability due to low hardness, low yield strength, and moderate elongation. It can be ground and polished readily using conventional methods. Because the physical properties of the alloy are not affected by the casting variables (casting temperature and alloy cooling rate) and by the porcelain firing schedules, the alloy maintains its excellent burnishing and polishing characteristics at all times.

Casting temperature, mold cooling rate (air cooling vs. water quenching of the mold), and alloy cycling during porcelain application do not alter the physical properties of the alloy. The alloy ductility can, however, by improved by one variable—mold temperature. Higher mold temperatures appear to increase the elongation and decrease the yield strength as shown below.

|  | Mold Temperature | |
|---|---|---|
|  | 1600° F. | 1800° F. |
| Elongation (%) | 3–6 | 7–11 |
| 0.02% Yield Strength (PSI) | 45,000 | 38,000 |

The alloy exhibits excellent oxidation properties and is readily compatible with all commercially available porcelains. The alloy is basically technique insensitive in that it does not require preconditioning in the furnace (degassing and heat treating at elevated temperatures). Furthermore, it needs no special bonding agent to enhance the procelain-to-metal adhesion, as is required by other conventional alloys. On the other hand, if the operator feels more confident in using a bonding agent, it would in no way affect the porcelain-to-metal adhesion adversely.

Typical properties of the alloy are as follows:

| 0.02% Yield Strength | 45,000 PSI |
|---|---|
| 0.2% Yield Strength | 55,000 PSI |
| Ultimate Tensile Strength | 90,000 PSI |
| % Elongation | 5–20 |
| Elastic Modulus (Young's) | $27 \times 10^6$ PSI |
| Coefficient of Thermal Expansion | $17.2 \times 10^{-6}$ in/in/°C. |
| Brinell Hardness Number | 190–205 |
| Knoup Hardness Number | 200–235 |

The ease of melting (castability) characteristic of the alloy is obtained by avoiding the formation of gamma phase' ($Ni_3Al$, Ti) which forms a tenacious oxide film over the molten alloy and makes it sluggish and prone to overmelting and thus even more sluggish and difficult to cast. The ease of finishing (grinding and polishing) characteristic of the alloy is obtained by reducing or avoiding the use of very strong solid-solution and precipitation hardners such as aluminum and titanium, and using such weak strengtheners such as iron and columbium. The corrosion resistance characteristic of the alloy is obtained by using a rather high concentration of chromium. The high and consistant porcelain bond to metal is obtained by the formation during porcelain firing of preferred oxides of iron, columbium and molybdenum.

The insensitivity of the alloy properties to various casting, handling and porcelain firing variables is not well understood, but is most probably due to the relatively low concentration of aluminum and the presence of $Ni_3Cb$, and carbides of columbium, molybdenum and chromium. The markedly improved melt cleanliness of the alloy is due to the moderate to relatively high carbon content. The small addition of aluminum also contributes to the alloy cleanliness, although it also increases the alloys microhardness.

The addition of silicon and carbon also contributes to the fluidity of the melt. The presence of the carbon is most critical to the melt cleanliness.

The alloy of the desired composition is cast at about 2750° F. by either induction melting or by oxygen/gas torch at oxygen pressures of about 40-50 PSIG. A multiorifice oxygen/gas melting tip is used on the torch. By either method, up to about 30 grams of alloy is rapidly melted in about 60 to 80 seconds when it is ready to cast into a ceramic mold. The lost wax technique is employed to cast the dental restorations. First, a fugitive wax pattern or replica of the would-be restoration is made and invested in a dental high-heat phosphate bonded investment. This ceramic mold is then heated to about 1600°-1800° F. to eliminate the wax and to attain adequate mold strength. The mold is then placed into either an induction or a torch-melt centrifugal casting machine, and molten alloy is then cast by centrifugal force.

Although most conventional alloys now available require some form of heat treatment or special bonding agents before applying porcelain, the alloy of the present invention does not require either procedure. Moreover, such procedures, if favored and utilized by a laboratory technician, would not adversely affect the properties or the performance of the alloy.

A chromium content of about 10-20 percent is generally held to be essential for good corrosion resistance. The other major function of the chromium is to provide oxidation resistance to the alloy.

Conventional complex nickel-alloys are strengthened by the formation of solid solution matrix (gamma phase) and coherent gamma' precipitate phase. As observed above, alloys with phases containing aluminum and titanium form tenacious oxide films on the molten metal and are generally very sluggish in their melting behavior. Thus, alloys containing moderate to high aluminum and titanium contents cannot be cast satisfactorily using an oxygen/gas torch. For alloys of the present invention the addition of columbium improves the castability considerably when using either air induction or torch melting procedures. In this instance the oxide film on the molten alloy is easily broken during melting.

The addition of small amounts of carbon and aluminum improve the cleanliness of the melt without affecting the physical properties adversely. A preferred carbon content of 0.05 to 0.5 percent and an aluminum content of up to 2 percent are preferred.

The columbium, although forming a precipitate ($Ni_3Cb$) contributes to the hardness and strength of the alloy, but less than that of gamma' phase ($Ni_3Al,Ti$). Thus, the hardness and strength of the alloy of the present invention, due to solid-solution hardening of gamma phase (Ni, Cr, Mo) and precipitation hardening of $Ni_3Cb$ phase, are much lower than conventional dental alloys containing a moderate to high content of aluminum and titanium. The addition of about 2 to 6 percent molybdenum assures satisfactory development of a primary matrix gamma phase. A 4 to 6 percent columbium content, and 3 to 6 percent iron content has been found to be satisfactory for both lower hardness and strength, and excellent alloy compatibility with all major porcelains.

The porcelain bond strength with the alloy depends upon the presence of suitable oxides on the alloy surface and the alloy compatibility with the porecelains (coefficient of thermal expansion). Porcelains have the best bond when under compression. To break the procelain bond, the stresses first must exceed the compression which the porcelain is under. It should be noted that the alloy not only provides greater thermal expansion so that it is compatible with most procelains, but the oxides of iron, columbium and molybdenum more than assure a satisfactory porcelain bond. This is one of the reasons why the alloy of the present invention does not need any particular heat treatment or bonding agent prior to applying the porcelain.

The following three alloys were made in a quartz crucible by the induction melting technique using an inert argon atmosphere, and are representative of typical alloys of the present invention.

EXAMPLE 1

|  | Percent by Weight | |
|---|---|---|
| Chromium | 14.0 | |
| Molybdenum | 5.0 | 0.2% Yield Strength = 44,500 PSI |
| Iron | 3.0 | Tensile Strength = 98,000 PSI |
| Columbium | 5.0 | % Elongation = 21% |
| Silicon | 1.0 | |
| Carbon | 0.12 | |
| Nickel | Balance | |

EXAMPLE 2

|  | Percent by Weight | |
|---|---|---|
| Chromium | 14.0 | |
| Molybdenum | 10.0 | |
| Iron | 6.0 | 0.2% Yield Strength = 49,000 PSI |
| Columbium | 5.0 | Tensile Strength = 98,000 PSI |
| Silicon | 1.0 | % Elongation = 24% |
| Carbon | 0.12 | |
| Nickel | Balance | |

EXAMPLE 3

|  | percent by Weight | |
|---|---|---|
| Chromium | 17.10 | |
| Molybdenum | 4.60 | |
| Iron | 6.00 | 0.2% Yield Strength = 55,000 PSI |
| Columbium | 5.80 | Tensile Strength = 91,000 PSI |
| Aluminum | 1.00 | % Elongation = 5% |

-continued

|  | percent by Weight |  |
|---|---|---|
| Silicon | 1.55 | Knoop Hardness = 235 |
| Carbon | 0.25 | |
| Nickel | Balance | |

A particularly preferred alloy composition range which has been found to give a desirable combination of physical properties for use as a crown and bridge alloy is as follows:

|  | Percent by Weight |
|---|---|
| Chromium | 17–18 |
| Molybdenum | 4–5 |
| Iron | 5–6 |
| Columbium | 4.5–6.0 |
| Aluminum | 0.5–1.2 |
| Silicon | 1.4–2.0 |
| Carbon | 0.2–0.4 |
| Nickel | Balance |

A total of 43 samples were prepared using the alloy of Example III with one of two commercial porcelains in order to evaluate the porcelain bond to metal. Fifteen samples used the alloy of Example III with Ceramco ® porcelain available commercially from Ceramco Inc., Division of Johnson & Johnson and 28 samples used the alloy of Example III with Vita porcelain available commercially from Unitek Corporation of Monrovia, California.

The porcelain bond was determined by testing the 43 samples under the shear mode according to the procedure described by Dr. Kamal Asgar of the University of Michigan in a paper presented in 1976 to the International Association for Dental Research in Miami, Florida. This paper is available upon request from the American Association for Dental Research, 734 15th Street N.W., Suite 809, Washington, D.C. 20005, and is incorporated herein by reference.

The average bond strength of the 15 samples using the alloy bonded to Ceramco porcelain ranged from about 10,700 to 12,730 psi. The average bond strength of the 28 samples using the alloy bonded to Vita porcelain ranged from about 10,325 to 10,800 psi. The bond strength exhibited by the alloy of the present invention compares favorably with the bond strength of other commercially available crown and bridge alloys. In addition, the alloy of the present invention showed a desirable hardness in the range of 230 to 240 Knoop Hardness and exhibited no significant reaction with the crucible during melting.

Other modifications and ramifications of the present invention would appear to those skilled in the art upon reading this disclosure. These are also intended to be within the scope of this invention.

What is claimed is:

1. A corrosion resistant biocompatible dental alloy which exhibits good porcelain to metal bond strength which consists of the following constituents:

|  | Percent by Weight |
|---|---|
| Chromium | 10–20 |
| Molybdenum | 4–10 |
| Iron | 3–6 |
| Columbium | 2–6 |
| Aluminum | up to 2.0 |
| Silicon | 1.0–3.0 |
| Carbon | 0.05–0.5 |
| Nickel | Balance. |

2. A dental alloy which consists essentially of the following constituents:

|  | Percent by Weight |
|---|---|
| Chromium | 17.10 |
| Molybdenum | 4.60 |
| Iron | 6.00 |
| Columbium | 5.80 |
| Aluminum | 1.00 |
| Silicon | 1.55 |
| Carbon | 0.25 |
| Nickel | Balance. |

3. A dental alloy which consists of the following constituents:

|  | Percent by Weight |
|---|---|
| Chromium | 14.0 |
| Molybdenum | 5.0 |
| Iron | 3.0 |
| Columbium | 5.0 |
| Silicon | 1.0 |
| Carbon | 0.12 |
| Nickel | Balance. |

4. A dental alloy which consists essentially of the following constituents:

|  | Percent by Weight |
|---|---|
| Chromium | 14.0 |
| Molybdenum | 10.0 |
| Iron | 6.0 |
| Columbium | 5.0 |
| Silicon | 1.0 |
| Carbon | 0.12 |
| Nickel | Balance. |

5. A corrosion resistant biocompatible dental alloy which exhibits good porcelain to metal bond strength which consists essentially of the following constituents:

|  | Percent by Weight |
|---|---|
| Chromium | 17–18 |
| Molybdenum | 4–5 |
| Iron | 5–6 |
| Columbium | 4.5–6.0 |
| Aluminum | 0.5–1.2 |
| Silicon | 1.4–2.0 |
| Carbon | 0.2–0.4 |
| Nickel | Balance |

* * * * *